United States Patent [19]
Bare et al.

[11] 3,987,185
[45] Oct. 19, 1976

[54] METHOD OF TREATMENT USING 1-OXO-1H-2-BENZOPYRAN-3-CARBOXYLIC ACID DERIVATIVES

[75] Inventors: Thomas M. Bare, Milwaukee; John T. Suh, Mequon, both of Wis.

[73] Assignee: Richardson-Merrell Inc., Wilton, Conn.

[22] Filed: Dec. 20, 1974

[21] Appl. No.: 534,730

Related U.S. Application Data

[63] Continuation-in-part of Ser. No. 414,993, Nov. 12, 1973, abandoned.

[52] U.S. Cl............................ 424/279; 424/281; 424/283
[51] Int. Cl.²................................ A61K 31/335
[58] Field of Search.............. 424/279, 281, 283

[56] References Cited
UNITED STATES PATENTS

| | | | |
|---|---|---|---|
| 3,008,970 | 11/1961 | Vander Stelt.................... | 260/343.2 |
| 3,733,338 | 5/1973 | Kimura et al...................... | 424/279 |
| 3,786,071 | 1/1974 | Cairns et al........................ | 424/283 |
| 3,816,470 | 6/1974 | Tronche et al.................... | 424/283 |
| 3,849,446 | 11/1974 | Strandtmann...................... | 424/283 |
| 3,862,143 | 1/1975 | Klutchko et al.................... | 424/283 |
| 3,864,493 | 2/1975 | Cairns et al........................ | 424/283 |
| 3,879,544 | 4/1975 | Reisner et al...................... | 424/337 |
| 3,883,653 | 5/1975 | Barth.................................. | 424/251 |
| 3,885,038 | 5/1975 | Pfister et al....................... | 424/283 |

OTHER PUBLICATIONS

Fisons Product Brochure, "Intal," July 1974, 2 pages.

*Primary Examiner*—Norman A. Drezin
*Attorney, Agent, or Firm*—William J. Stein; Eugene O. Retter; George W. Rauchfuss, Jr.

[57] ABSTRACT

The method comprises administering to an animal an amount of substituted-1-oxo-1H-2-benzopyran-3-carboxylic acid effective to inhibit antigen-antibody reaction in said animal. Representative of the compounds that can be used in the method is sodium 1-oxo-1H-2-benzopyran-3-carboxylate.

6 Claims, No Drawings

METHOD OF TREATMENT USING 1-OXO-1H-2-BENZOPYRAN-3-CARBOXYLIC ACID DERIVATIVES

RELATED CASE

This application is a continuation-in-part of my copending application, Ser. No. 414,993, filed Nov. 12, 1973, now abandoned.

BACKGROUND OF THE INVENTION

The compound disodium cromoglycate (Intal), which inhibits the release of spasmogens from antigen-antibody reactions, is effective in the treatment of asthma and other allergic diseases. Numerous articles have been issued which report the clinical results obtained with disodium cromoglycate. In addition, the following United States Patents have issued describing disodium cromoglycate and related compounds: U.S. Pat. Nos. 3,567,741; 3,706,768; 3,705,945; 3,419,578; 3,686,412; 3,671,625; 3,718,668; 3,673,218; 3,686,320; and 3,634,582.

DESCRIPTION OF THE INVENTION

The present invention relates to a method of preventing allergic reactions in animals and comprises administering to said animals a safe and effective amount of a compound of the formula:

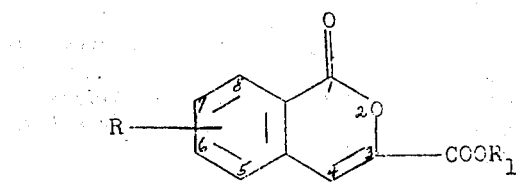

in which R is hydrogen or lower alkoxy of 1 to 4 carbon atoms, methoxy, isopropoxy and t-butoxy, and $R_1$ is hydrogen or sodium.

Representative of the compounds which may be employed in the method are the following:

1-Oxo-1H-2-benzopyran-3-carboxylic acid,
Sodium 1-oxo-1H-2-benzopyran-3-carboxylate,
Sodium 8-methoxy-1-oxo-1H-2-benzopyran-3-carboxylate,
Sodium 8-methoxy-isocoumarin-3-carboxylate,
Sodium 7-methoxy-1-oxo-1H-2-benzopyran-3-carboxylate,
Sodium 6-methoxy-1-oxo-1H-2-benzopyran-3-carboxylate,
Sodium 5-methoxy-1-oxo-1H-2-benzopyran-3-carboxylate,
Sodium 8-ethoxy-1-oxo-1H-2-benzopyran-3-carboxylate,
Sodium 3-isopropoxy-1-oxo-1H-2-benzopyran-3-carboxylate, and
Sodium 8-tert-butoxy-1-oxo-1H-2-benzopyran-3-carboxylate.

The above compounds may be prepared as described in the examples or in the literature. The preparation of related compounds is described in U.S. Pat. No. 3,008,970, as well as in the article by H. W. Johnston, et al., in *The Journal of Organic Chemistry*, Vol. 13, page 477 (1948).

The aforementioned compounds have been shown to inhibit the release of spasmogens from antigen-antibody reactions such as occur in the rat during the PCA (passive cutaneous anaphylaxis) test described by Ogilvie in *Immunology*, Vol. 12, page 113 (1967). The compound sodium 1-oxo-1H-2-benzopyran-3-carboxylate, when given intravenously, was found to be as potent as disodium cromoglycate in inhibiting the PCA reaction in sensitized rats. It has been found that this test gives reliable qualitative indications of the ability of the compounds being tested to inhibit antibody-antigen reactions in man. Therefore, the compounds are of value in the treatment of conditions in which the extrinsic antigen combination with a reaginic antibody is primarily responsible, for example, extrinsic asthma, hay fever, urticaria, eczema or atopic dermatitis.

In animal behavior tests the aforementioned compounds were found to possess very low toxicity values, that is, they had $LD_{50}$ values of at least 500 mg/kg of the compound, in terms of the free acid, when administered intraperitoneally.

The inventive method is preferably carried out employing the active ingredient in the form of a pharmaceutical composition which contains, in addition, suitable pharmaceutical carriers and excipients. The compositions may also contain other medicinal agents such as bronchodilators, antihistamines or tranquilizers. Suitable dosage forms include tablets, capsules, syrups, emulsions and powders for inhalation.

A preferred form of administration is by inhalation. The compositions employed for inhalation will generally be in the form of a powder or an aerosol spray. The following are representative formulations for inhalation:

| Aerosol Formulation | |
| --- | --- |
| Sodium 1-oxo-1H-2-benzopyran-3-carboxylate | 2% |
| Sodium dioctyl sulphosuccinate | 0.004% |
| Propellant | ad 100% |
| Solid Powder Formulation | |
| Each dosage unit contains: | |
| Sodium 1-oxo-1H-2-benzopyran-3-carboxylate | 20 mg. |
| Lactose | 15 mg. |

The dosage at which the active ingredient is administered may vary within a wide range depending upon the physical condition of the patient and the allergic reaction being treated. Generally, however, a suitable oral dosage range is from 20 to 1500 mg. and a suitable inhalation dosage range is from 1 to 50 mg.

The following examples further illustrate the invention:

EXAMPLE 1

Phthalide-3-hydroxyacetic acid

One hundred grams (700 mM) of calcium hypochlorite is triturated with 100 ml. of water and the liquid decanted and filtered through a Buchner funnel to remove a small amount of a finely dispersed solid. The undissolved calcium hypochlorite is triturated two additional times with 150 ml. portions of water, each time decanting and filtering the water solution. The combined filtrates are cooled to 0° and added in small portions to a stirred, cooled (5°–10°) mixture of 9.0 g. (56.8 mM) of 1,2-naphthoquinone and enough water to make a thick paste. The addition is regulated so that the temperature of the reaction mixture never exceeds 10°. A tan solid forms during the addition. After the addition is complete, the mixture is filtered and the collected solid washed with 30 ml. of cold water and several portions of acetone. The solid is air-dried to give 10.19 g. of the calcium salt of phthalide-3-hydroxyacetic acid. The solid is added portionwise to a hot solution of 4ml. of concentrated hydrochloric acid in 50 ml. of water. The hot solution is filtered and, on cooling, tan crystals of phthalide-3-hydroxyacetic acid precipitate, m.p. 207°–209°.

EXAMPLE 2

1Oxo-1H-2-benzopyran-3-carboxylic acid

A stirred mixture of 1.00 g. (4.8 mM) of the hydroxy acid of Example 1, 0.50 g. (6.1 mM) of sodium acetate, and 11 ml. of acetic anhydride is warmed to 160°. During the heating the solids dissolve and a voluminous white precipitate forms. The mixture is allowed to cool and is dissolved in 35 ml. of water to which concentrated hydrochloric acid is then added. The strongly acid solution is cooled (0°) for 3 hours, and filtered to separate the carboxylic acid 1-oxo-1H-2-benzopyran-3-carboxylic acid as a pale yellow solid, m.p. 243.5°–244.5°.

Anal. Calcd. for $C_{10}H_6O_4$: C, 63.17; H, 3.18. Found: C, 63.08; H, 3.26.

EXAMPLE 3

Sodium 1-oxo-1H-2-benzopyran-3-carboxylate

To a stirred suspension of 4.000 g. (21.04 mM) of 1-oxo-1H-2-benzopyran-3-carboxylic acid in 225 ml. of distilled water is added portionwise 1.768 g. (21.04 mM) of sodium bicarbonate. After stirring for 0.5 hour, all the solids dissolve and the solution is frozen and freeze-dried to give 4.40 g. of the sodium salt, sodium 1-oxo-1H-2-benzopyran-3-carboxylate, as a fluffy white solid, m.p. 327°.

Anal. Calcd. for $C_{10}H_5NaO_4.4/5H_2O$: C, 53.01; H, 2.94. Found: C, 52.75; H, 2.73.

EXAMPLE 4

4-(2-Carboxy-3-methoxybenzylidene)-2-phenyl-5(4H)-oxazolone

To a stirred solution of 0.65 g. (11.5 mM) of potassium hydroxide in 23 ml. of ethanol is added 2.07 g. (11.5 mM) of 6-methoxyphthalaldehydic acid. To the resulting cooled (10°) milky suspension is added 1.89 g. (11.75 mM) of 2-phenyl-5-oxazolone. The mixture is warmed to 25° and stirred at this temperature for 35 minutes. A light orange precipitate forms. The mixture is made acidic with 3.45 ml. of 4N sulfuric acid and the resulting mixture kept at 0° for 1.5 hours and filtered. The collected solid is washed with a small amount of cold ethanol and then hexane. Air-drying gives the oxazolone 4-(2-carboxy-3-methoxybenzylidene)-2-phenyl-5(4H)-oxazolone as a yellow solid, m.p. > 320°.

EXAMPLE 5

8-Methoxy-1-oxo-1H-2-benzopyran-3-carboxylic acid

A solution of the oxazolone of Example 4 (1.80 g., 5.57 mM) and 3.06 g. of sodium hydroxide in 15.2 ml. of water is refluxed under nitrogen for two hours. The resulting solution is cooled, acidified with concentrated hydrochloric acid, and refluxed for 0.5 hour. The solution is cooled and filtered to separate the precipitated solids. The dried solid is triturated with 2 ml. of cold methanol (to remove benzoic acid) and filtered to separate the product, m.p. 251°–253°. Recrystallization from 12 ml. of methanol (charcoal) gives 8-methoxy-1-oxo-1H-2-benzopyran-3-carboxylic acid as a white solid, m.p. 255°–256°.

EXAMPLE 6

Sodium 8-methoxy-1-oxo-1H-2-benzopyran-3-carboxylate

To a stirred suspension of the carboxylic acid of Example 5 (3.7529 g., 17.05 mM) in 225 ml. of distilled water is added 1.4324 g. (17.05 mM) of sodium bicarbonate. After stirring 0.75 hour, the solution is filtered and freeze-dried to give a pale green solid. The solid is dried at 100° under vacuum for four hours to give sodium 8-methoxy-1-oxo-1H-2-benzopyran-3-carboxylate as a pale green solid, m.p. 244°.

Anal. Calcd. for $C_{11}H_7NaO_5.\frac{1}{2}H_2O$: C, 52.60; H, 3.22. Found: C, 52.92; H, 2.99.

We claim:

1. A method of inhibiting the release of spasmogens from antigen-antibody reactions in an animal in need thereof which comprises administering to said animal a safe and effective amount of a compound having the formula:

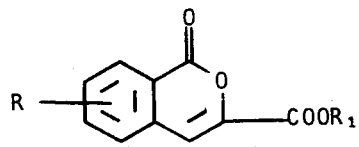

in which R is hydrogen or lower alkoxy, and $R_1$ is hydrogen or sodium.

2. The method of claim 1 in which the compound administered is 1-oxo-1H-2-benzopyran-3-carboxylic acid.

3. The method of claim 1 in which the compound administered is sodium 1-oxo-1H-2-benzopyran-3-carboxylate.

4. The method of claim 1 in which the compound administered is sodium 8-methoxy-1-oxo-1H-2-benzopyran-3-carboxylate.

5. The method of claim 1 in which the compound is administered by inhalation.

6. The method of claim 1 in which the compound is administered orally.

* * * * *

UNITED STATES PATENT AND TRADEMARK OFFICE
CERTIFICATE OF CORRECTION

PATENT NO. : 3,987,185
DATED : October 19, 1976
INVENTOR(S) : Thomas M. Bare and John T. Suh It is certified that error appears in the above–identified patent and that said Letters Patent are hereby corrected as shown below:

Column 1, line 57, "Sodium 3-isopropoxy" should read "Sodium 8-isopropoxy"

Signed and Sealed this

Twenty-second Day of March 1977

[SEAL]

Attest:

RUTH C. MASON
*Attesting Officer*

C. MARSHALL DANN
*Commissioner of Patents and Trademarks*